United States Patent [19]

Gauthier et al.

[11] Patent Number: 4,820,856

[45] Date of Patent: Apr. 11, 1989

[54] PROCESS FOR THE PRODUCTION OF ALKYL THIOCHLOROFORMATES

[75] Inventors: Patricia Gauthier, Cerny; Thierry Malfroot, Saintry sur Seine; Jean-Pierre Senet, Herbeauvilliers-Buthiers, all of France

[73] Assignee: Societe Nationale des Poudres et Explosifs, Paris, France

[21] Appl. No.: 108,996

[22] Filed: Oct. 16, 1987

[30] Foreign Application Priority Data

Oct. 17, 1986 [FR] France .................................. 8614407

[51] Int. Cl.$^4$ .............................................. C07C 68/02
[52] U.S. Cl. ..................................................... 558/249
[58] Field of Search ........................................ 558/249

[56] References Cited

U.S. PATENT DOCUMENTS

| | | | |
|---|---|---|---|
| 3,277,143 | 10/1966 | Tilles | 558/249 |
| 4,268,456 | 5/1981 | Keim et al. | 558/249 |
| 4,273,725 | 6/1981 | Cook, Jr. | 558/249 |
| 4,340,746 | 7/1982 | Semler et al. | 558/249 |

FOREIGN PATENT DOCUMENTS

| | | | |
|---|---|---|---|
| 0053981 | of 0000 | European Pat. Off. | 558/249 |
| 2462423 | of 0000 | France | 558/249 |

OTHER PUBLICATIONS

Dehmlow, et al., Phase Transfer Catalysis, Verlag Chemie, Weinheim, (1980), pp. 46-48.

Primary Examiner—John M. Ford
Assistant Examiner—Robert C. Whittenbaugh
Attorney, Agent, or Firm—Burns, Doane, Swecker & Mathis

[57] ABSTRACT

The subject of the invention is a new process for the preparation of alkyl thiochloroformates.

The process according to the invention consists in reacting phosgene with a mercaptan in the presence of a catalyst which is a hexaalkylguanidinium chloride or the corresponding hydrochloride of general formula:

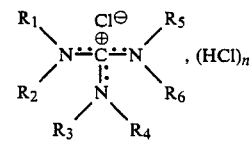

in which $R_1$, $R_2$, $R_3$, $R_4$, $R_5$ and $R_6$ represent alkyl radicals containing 1 to 4 carbon atoms and in which n may take either the value 0 or the value 1.

The preferred catalysts are hexamethylguanidinium chloride and its hydrochloride.

The process according to the invention enables very pure alkyl thiochloroformates to be obtained with milder operating conditions and simplified purification operations.

7 Claims, No Drawings

PROCESS FOR THE PRODUCTION OF ALKYL THIOCHLOROFORMATES

The subject of the invention is a new process for the preparation of thiochloroformates.

The preparation of thiochloroformates by reacting phosgene with a mercaptan in the presence of a catalyst has been known for a long time.

The reaction scheme is as follows:

$$R-SH + COCl_2 \xrightarrow{catalyst} R-S-\underset{\underset{O}{\|}}{C}-Cl + HCl$$

The presence of a catalyst is indispensible for obtaining thiochloroformate under economically acceptable conditions. Activated charcoal has been widely used, but it has several disadvantages. Its recycling is difficult because it loses its catalytic power. Additionally, fine particles remain in suspension in the final product, making it necessary to carry out a purification, which is difficult, at the end of the synthesis.

Several types of organic catalysts have also been proposed:

amides (U.S. Pat. Nos. 3,277,143 and 4,340,746);

secondary amines and their hydrochlorides (U.S. Pat. No. 4,273,725 and French Pat. No. 2,462,423);

tertiary amines (U.S. Pat. No. 3,277,143);

quaternary ammonium salts (U.S. Pat. No. 4,268,456 and French Pat. No. 2,462,423);

some anion exchange resins (French Pat. No. 2,462,423); and ureas and their reaction products with phosgene or a thiochloroformate (U.S. Pat. No. 4,340,746).

All these catalysts have the following disadvantages to variable extents:

in order to obtain a sufficient reaction rate, at least 0.01 molar equivalent of catalyst is required. This involves a purification by distillation at the end of the reaction. Now, this distillation is very difficult to carry out in the case of higher thiochloroformates.

the yields obtained are variable and sometimes low.

the use of most of these catalysts gives rise to the formation of hindersome byproducts (carbamyl chlorides, tars, sludges and the like), making it difficult and tedious to purify the finished products.

Therefore, there is a need, which has not been met, to make available a catalyst which is efficient and which does not have the disadvantages listed.

The subject of the present invention is a process for the production of thiochloroformates, using such catalysts.

The process according to the invention is a process for the production of alkyl thiochloroformates by the action of phosgene on a mercaptan, in the presence of a catalyst, characterized in that the said catalyst is a hexaalkylguanidinium chloride or the corresponding hydrochloride, of general formula:

$$\begin{array}{c} R_1 \\ \diagdown \\ R_2 \end{array} N \overset{Cl^{\ominus}}{\underset{\underset{R_3}{|}}{\overset{\oplus}{=}}} \overset{R_5}{\underset{N}{\diagup}} , (HCl)_n$$

in which $R_1$, $R_2$, $R_3$, $R_4$, $R_5$ and $R_6$ are identical or different and represent $C_1$ to $C_4$ alkyl radicals and in which n may take the values 0 or 1.

An advantage of these catalysts is that the quantity required is much lower than those described in other processes. In the process according to the invention, this quantity is between $10^{-3}$ and $10^{-2}$ molar equivalent of catalyst relative to the thiol.

Therefore, the thiochloroformates thus obtained contain virtually no catalyst as impurities.

In many cases, this advantage enables a distillation which is particularly difficult or even impossible to achieve without degradation, to be avoided. This advantage applies especially to thiochloroformates, the alkyl radical of which contains between 6 and 20 carbon atoms and preferentially between 6 and 12 carbon atoms.

According to a particularly advantageous variant of the invention, $R_1$, $R_2$, $R_3$, $R_4$, $R_5$ and $R_6$ are identical and represent the methyl radical.

The invention is described below in detail.

The process according to the invention is therefore a process for the synthesis of thiochloroformates by reacting phosgene with a mercaptan or a thiol, in the presence of a catalyst, according to the reaction scheme:

$$RSH + COCl_2 \xrightarrow{catalyst} R\underset{\underset{O}{\|}}{S}CCl + HCl,$$

in which C, H, O, S and Cl represent carbon, hydrogen, oxygen, sulphur and chlorine respectively, and R represents an alkyl residue.

The process according to the invention can be applied to thiols RSH, the radical R of which is a straight-chain or branched saturated alkyl residue containing from 1 to 20 carbon atoms.

The catalyst employed is a hexaalkylguanidinium chloride or the corresponding hydrochloride of general formula (I)

$$\begin{array}{c} R_1 \\ \diagdown \\ R_2 \end{array} N \overset{Cl^{\ominus}}{\underset{\underset{R_3}{|}}{\overset{\oplus}{=}}} \overset{R_6}{\underset{N}{\diagup}} , (HCl)_n \quad (I)$$

in which $R_1$, $R_2$, $R_3$, $R_4$, $R_5$ and $R_6$, which may be identical or different, represent alkyl radicals containing from 1 to 4 carbon atoms and in which n may take either the value 0 or the value 1.

The catalysts which are preferred within the scope of the present invention are those in which the six radicals $R_1$, $R_2$, $R_3$, $R_4$, $R_5$ and $R_6$ are identical and represent the methyl group, i.e. the hexamethylguanidinium chloride or its hydrochloride of general formula (II):

$$\begin{array}{c} CH_3 \\ \diagdown \\ CH_3 \end{array} N \overset{Cl^{\ominus}}{\underset{\underset{CH_3}{|}}{\overset{\oplus}{=}}} \overset{CH_3}{\underset{N}{\diagup}} , (HCl)_n \quad (II)$$

with n=0 or 1.

In fact, the compounds of formula (II) which are employed as catalysts for the phosgenation of mercaptans RSH, the radical R of which contains a number of carbon atoms between 6 and 20, precipitate at the end of the reaction, after the removal of phosgene by degassing. Therefore, in this case, it is possible to obtain perfectly pure thiochloroformates, free from any trace of catalyst, simply by filtering.

The catalysts according to the invention which are, moreover, described as catalysts for the phosgenation of acids into acid chlorides in the French Patent Application No. 85/11,248 in the name of the Applicant Company, may be prepared in a known manner according to several processes. For example, it is possible to prepare them starting with a urea or thiourea which is phosgenated so as to obtain chloroformamidinium chloride (Chem. Ber. 97, p 1232, 1964), which is then made to react with an amine (Synthesis 1983, 11, pages 904–905); or by reacting a thiourea with a carbamyl chloride (Liebigs Ann. Chem., 1984, pages 108–126); or alternatively, starting with pentaalkylguanidines which are reacted with a halogenated derivative (Houben Weyl, VIII, pages 100 and 186, 1952), the pentaguanidines themselves being obtained by reacting an isocyanatodihalide with a secondary amine (French Pat. No. 1,453,438).

The hydrochlorides may be prepared either by adding hydrochloric acid to hexaalkylguanidinium chloride, or, when a method using a chloroformamidinium chloride is employed, by reacting this formamidinium chloride with a secondary amine, followed, without separation of the products obtained, by a phosgenation.

The phosgenation reaction of mercaptans or thiols according to the invention may be carried out in the absence of solvent, or in the presence of a solvent which is inert towards phosgene and capable of dissolving both the mercaptan and the phosgene. This solvent may be a chlorinated aliphatic solvent such as dichloromethane, or an aromatic solvent such as chlorobenzene, toluene or a xylene. Toluene is well suited.

Nevertheless, the preferred solution is the phosgenation of mercaptan without solvent.

According to another advantage of the invention, the reaction may be carried out at a moderate temperature, of between 30° C. and 50° C., because of the high efficiency of the catalysts employed.

In general, the reaction is carried out with an excess of phosgene in order to avoid the formation of interfering products such as, for example, carbonates. The reaction according to the invention is preferably carried out in the presence of a 5 to 10 mole % excess of phosgene.

By virtue of the process according to the invention, alkyl thiochloroformates which are virtually free from impurities are obtained, with milder operating conditions and simplified purification operations.

Additionally, the catalyst can be easily recycled, especially when it is recovered by filtration.

Thiochloroformates are very well known compounds which have many applications, for example as intermediates in plant protection industries. The process according to the invention makes it possible to obtain thiochloroformates leading to thiocarbamates which form part of a large number of herbicidal and pesticidal compositions. According to a particularly advantageous embodiment of the process, it is possible to obtain higher alkyl thiochloroformates which have been very difficult or even impossible to obtain until now by known processes.

The process according to the invention is particularly well suited to the preparation of n-octyl thiochloroformate of formula (III)

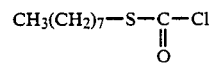

which is an important intermediate in the pesticide industry.

EXAMPLE

Preparation of n-octanethiol chloroformate

This example relates to the synthesis of n-octyl thiochloroformate by reacting n-octanethiol with phosgene in the presence of hexamethylguanidinium chloride hydrochloride as catalyst.

A/ Preparation of the catalyst

The catalyst is prepared by the phosgenation of tetramethylurea so as to obtain tetramethylchloroformamidinium chloride, which is then reacted with dimethylamine, the procedure being completed by a phosgenation of the reaction mixture, according to the following scheme:

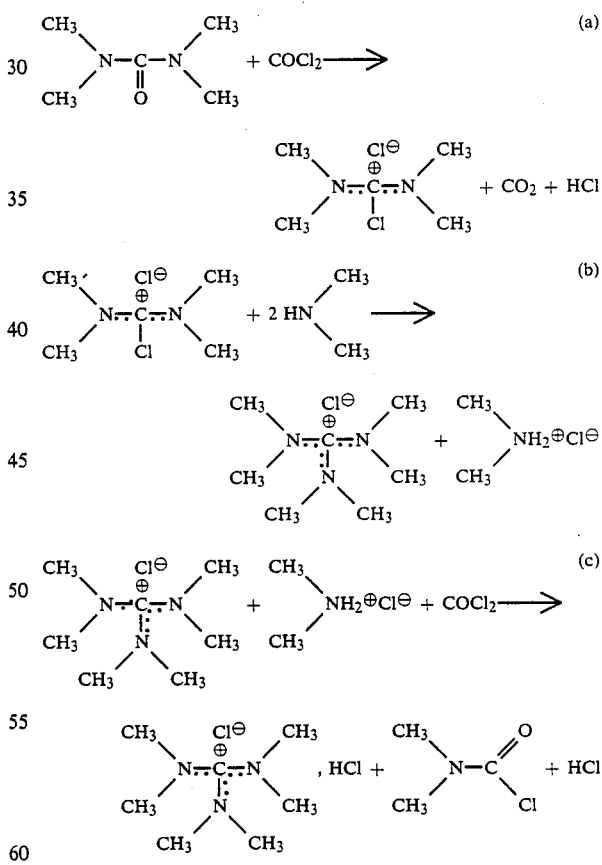

0.5 mole of tetramethylurea is phosgenated in 130 cm³ of 1,2-dichloroethane at 80° C. for three hours in the presence of a 25% molar excess of phosgene. After the addition of phosgene, stirring is maintained at 80° C. for four hours. The excess phosgene is then removed from the reaction medium by a degassing under reduced pressure.

1.1 moles of gaseous dimethylamine are added to the reaction medium above in a 500-ml reactor equipped with a mechanical stirrer, a thermometer, a condenser which uses a solid carbon dioxide-methylene chloride mixture and an inlet tube, in the course of two and a half hours. The reaction is highly exothermic and the temperature rises from 20° C. to 82° C.

The mixture is maintained stirred for one hour. The medium is heterogeneous, but easy to stir. The characteristic disappearance of the band for $C^{\oplus}$—N of chloroformamidinium at 1650 cm$^{-1}$ and the appearance of the bands for the guanidinium salt at 1580 cm$^{-1}$ and 1600 cm$^{-1}$ may be verified by infrared spectroscopy.

The reaction medium is then heated under reflux between 90° C. and 95° C. and 0.75 mole of gaseous phosgene is added in the course of two and a half hours. Stirring is then maintained for three and a half hours at a temperature of 90° C.

Analysis by infrared spectroscopy shows the presence of carbamyl chloride with a band at 1740 cm$^{-1}$. This compound is analysed by gas chromatography GC, with an internal standard. The end of reaction can thus be determined.

The excess phosgene is then removed by degassing under reduced pressure. After the removal of 1,2-dichloroethane at 12 mm of mercury, at a temperature of between 50° and 60° C., the residue obtained is taken up with 100 cm$^3$ of hexane. Hexamethylguanidinium chloride hydrochloride precipitates.

After filtering and washing with 2×200 cm$^3$ of hexane, the product is dried to constant weight under a vacuum of 1 mm of mercury at ambient temperature.

The product has the following characteristics:
Mass obtained: 104 g
Theoretical mass: 108 g
Yield: 96%
Melting point: 105° C. on Kofler bench
Hydrolysable chlorine content obtained: 31%
Theoretical hydrolysable chlorine content: 32.87%

B/ Preparation of n-octanethiol chloroformate 146 g (1 mole) of octanethiol and 0.324 g (0.0015 mole) of hexamethylguanidinium chloride hydrochloride are introduced into a 500-ml reactor with a condenser at −70° C. fitted from above. Gaseous phosgene (1.5 moles) is introduced, in the course of two hours, into the reaction mixture maintained at 37° C. (±2° C.). The addition being complete, stirring is continued for 3 hours at this temperature. The reaction is then complete.

After careful degassing at 30° C. at 30 mm of mercury, the catalyst which precipitates is separated from the thiochloroformate by filtering, after lowering the temperature of the reaction medium to 8°–10° C., through a SARTORIUS ® type filter with a 5 micrometer pore-size teflon sheet.

After washing the catalyst with hexane and drying under reduced pressure (1 mm of mercury) at ambient temperature, 0.3049 g of the catalyst is recovered, which amounts to 94% by mass of the quantity employed.

The n-octyl thiochloroformate which is obtained with a yield of 100% after separation of the catalyst, has the following characteristics:
Chlorine content: theoretical: 17.026% found: 17.03–17.08% (purity 100%).
Gas chromatography: no impurity
Infrared spectrometry: band C=0 to 1770 cm$^{-1}$
Colour: 20 APHA absence of suspended material after 2 h at −30° C. and 10 days at ambient temperature.

A recycling test of the catalyst recovered was carried out. When used at a rate of 0.13 mole %, it enabled a new batch of octanethiol to be phosgenated under the conditions above in 7 h 15 min (conversion rate: 99%).

I claim:

1. Process for the production of thiochloroformates, comprising: reacting phosgene with a mercaptan, in the presence of a catalyst, wherein said catalyst is a hexaalkylguanidinium chloride or the corresponding hydrochloride of general formula:

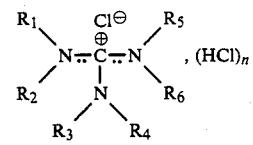

in which $R_1$, $R_2$, $R_3$, $R_4$, $R_5$ and $R_6$ are identical or different and represent $C_1$ to $C_4$ alkyl radicals, and in which n may take the values of 0 to 1.

2. Process according to claim 1, wherein $R_1$, $R_2$, $R_3$, $R_4$, $R_5$ and $R_6$ are identical and represent methyl.

3. Process according to claim 1 wherein the quantity of catalyst employed is between $10^{-3}$ and $10^{-2}$ equivalent relative to the thiol.

4. Process according to claim 1 wherein the reaction temperature is between 30° and 50° C.

5. Process according to claim 1 wherein said mercaptan is of the general formula R-SH in which R is a $C_6$ to $C_{20}$ alkyl or cycloalkyl radical.

6. Process according to claim 5, wherein said catalyst is the hexamethylguanidinium chloride or its hydrochloride, and wherein said catalyst is separated from the thiochloroformate at the end of the reaction by filtering.

7. Process according to claim 1 wherein the reaction is carried out with 5 to 10 mole % excess of phosgene.

* * * * *